(12) United States Patent
Porath

(10) Patent No.: US 6,668,187 B1
(45) Date of Patent: Dec. 23, 2003

(54) OPTICAL MAMMOGRAPHY

(75) Inventor: Asher Porath, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/744,879

(22) PCT Filed: Jul. 30, 1998

(86) PCT No.: PCT/IL98/00359

§ 371 (c)(1),
(2), (4) Date: Jun. 29, 2001

(87) PCT Pub. No.: WO00/06016

PCT Pub. Date: Feb. 10, 2000

(51) Int. Cl.[7] ................................................. A61B 6/00
(52) U.S. Cl. ...................... 600/476; 600/407; 250/358.1
(58) Field of Search ............................... 250/358.1, 339, 250/341, 360.1; 600/473, 476, 407; 128/664, 665

(56) References Cited

U.S. PATENT DOCUMENTS

| | | | |
|---|---|---|---|
| 4,515,165 A | * 5/1985 | Carroll | ........................ 600/475 |
| 4,767,928 A | 8/1988 | Nelson et al. | |
| 4,945,239 A | 7/1990 | Wist et al. | |
| 4,948,974 A | * 8/1990 | Nelson et al. | ............ 250/358.1 |
| 5,386,447 A | * 1/1995 | Siczek | .......................... 378/37 |
| 5,660,181 A | 8/1997 | Ho et al. | |
| 5,845,639 A | * 12/1998 | Hochman et al. | ............ 600/407 |
| 6,032,070 A | 2/2000 | Flock et al. | |
| 6,345,194 B1 | * 2/2002 | Nelson et al. | ............... 600/425 |

FOREIGN PATENT DOCUMENTS

| | | |
|---|---|---|
| EP | 0 280 418 A1 | 8/1988 |
| EP | 0 447 708 A2 | 9/1991 |
| GB | 2 111 794 B | 11/1985 |
| WO | WO 96/20638 A1 | 7/1996 |
| WO | WO 96/39925 A1 | 12/1996 |
| WO | WO 97/21114 A1 | 6/1997 |

OTHER PUBLICATIONS

Ertefai, S. et al.; "Spectral Transmittance and Constrast in Breast Diaphanography"; Med. Phys.; vol. 12; No. 4; pp. 393–400; Jul.–Aug. 1985.

Watmough, D.; "Transillumination of Breast Tissues: Factors Governing Optimal Imaging of Lesions"; Radiology; vol. 147; No. 1; pp. 89–92; Apr. 1983.

"Optical Mammography Offers Promise as Alternative to X–Ray Detection"; Biophotonics International; pp. 56–57; Jan.–Feb. 1996.

Cutler, M.; "Transilluminations an Aid in the Diagnosis of Breast Lesions with Special Reference to its Value in Cases of Bleeding Nipple," Jun. 1929; pp. 721–729; Surgery, Ginecology and Obstetrics: An International Magazine, Published Monthly; vol. 48, No. 6.

Navarro, G. A. et al.; "Contrast in Diaphanography of the Breast," Mar./Apr. 1988; pp. 181–187; Med. Phys.; vol. 15, No. 2.

\* cited by examiner

*Primary Examiner*—George Manuel
*Assistant Examiner*—Barry Pass
(74) *Attorney, Agent, or Firm*—Fenster & Company (57) ABSTRACT

Apparatus for imaging cross-sectional views of the inner structure of the breast, the apparatus comprising: a source of light (12) illuminating the breast situated at a first position of the breast a matching interface (19) situated, at a second position, on a surface of the breast, which reduces scatter caused by said surface; and an imaging detector (24) focused on a plane within the breast, through said matching interface.

28 Claims, 7 Drawing Sheets

OPTICAL MAMMOGRAPHY

RELATED APPLICATION

This application is a U.S. national filing of PCT Application 9 PCT/IL98/00359, filed Jul. 30, 1998.

FIELD OF THE INVENTION

This invention relates in general to imaging devices used to detect breast cancer and more particularly to such imaging devices known as transillumination devices which use non-ionizing radiation such as optical radiation to image the interior of the breast.

BACKGROUND OF THE INVENTION

Transillumination imaging devices and methods (sometimes referred to as "optical mammography") for diagnosis of breast lesions were first described in an article by Cutler in the Journal of Surgical Gynecology, Obstetrics Vol., 48:721 (1929). Transillumination imaging uses intensive non-ionizing radiation such as light that is detected after transmission through the breast and processed to provide image data from the interior of the breast.

The main motivating factor behind the use of transillumination for detection of breast cancer rather than x-rays has been the problems caused by the ionizing x-rays. For safety reasons it is recommended that the use of x-rays for detection of cancer generally be restricted to women age 40 and over and further be restricted to only one test per year. The use of non-ionizing radiation devices such as ultrasound or transillumination enables testing women under 40 as well as over 40 and is not restricted to use once per year. There are no negative safety repercussions derived from testing for breast cancer more than once a year using non-ionizing radiation.

U.S. Pat. No. 4,945,239 describes prior art transillumination devices and the problems inherent with such devices. An important problem with transillumination devices is that the low energy photons of the light beams are easily scattered and therefore produce blurred images. The transillumination prior art used many methods in attempting to reduce the scatter and to generally improve the transillumination images. However, the scatter reducing methods and devices described by the prior art are relatively complicated and difficult to use. For example, the aforementioned patent describes reducing scatter by using a pin hole box between the light source and the breast and again between the breast and the detector. This does reduce scatter, however, the pin hole boxes and light sources have to be very accurately aligned and even more detrimental is the fact that the procedure is time consuming because the pin hole boxes are used in a scanning regimen to image the breast interior.

U.S. Pat. No. 4,945,239 also describes using an unspecified marker that is opaque to an unspecified wavelength of light as a contrast agent Another method of reducing scatter is through the use of complicated optical lens systems or polarizing filters between the light source and the breast and between the breast and the detector.

Yet another prior art scatter reducing procedure uses mirrors. A semi-permeable mirror is used between the light source and the breast to transport light to the breast and to a detector in conjunction with a phase conjugated mirror that receives light that has traversed the breast. The phase conjugated mirror sends the light back through the breast to the semi-permeable mirror and the detector. Thus, the prior art faced the problem of light scattering when transillumination was used to detect cancer in breasts by providing complicated systems such as complicated lens systems, mirror systems and pin hole systems.

The great difficulty in discovering lesions embedded in breast tissue by transillumination was highlighted in a theoretical investigation by Navarro et al. described in the Medical Physics Journal 15:181 (1988). That study concluded that lesions of 0.5 centimeter in size would not be detected by transillumination if located deeper than 0.5 centimeters from the skin surface because of scatter caused by the skin surface interface.

A prior art system used "time of flight" analysis to distinguish light beams traversing the breast in a straight line from the source to the detector from scattered light.

In the patents listed and analyzed in the above mentioned patent it seems that only U.S. Pat. No. 4,767,928 discloses obtaining planar or tomographic images. The planar image is obtained by rotating the light beams around the breast. The prior art does not acquire images by focusing on different planes illuminated by the light traversing the breast. The patents in general merely examine the light that makes it through the breast and does the imaging based strictly on the intensity of light traveling through the breast detected after traveling through the breast wherein the intensity of the light is used to obtain mainly shadowgraph images based on absorption and scatter. Thus the detected light is light that was not absorbed by the tissue is imaged. Where absorption is high; then the cause of the high absorption is attributed to a possible lesion. Thus if a lesion exists at some level in the breast the detection of the lesion is hampered by scatter and by variations in the overlying and underlying structure of the breast all of which are imaged together.

More recently in transillumination apparatus, broad beam light sources referred to as "light torches" have been used for breast imaging.

Again, the main problem is scatter. Spatial resolution and contrast are lost because of scatter. U.S. Pat. No. 4,948,974 acquires image data by focusing the light coming into the breast onto points in the breast and then moving the light source to scan different planar sections within the breast and to detect the light from those planes. This patent mentions the use of single wavelength illumination to reduce scatter, in contrast to the prior art which uses broadband illumination.

UK patent GB 2 111 794 inter alia describes a system in which a breast is illuminated by a collimated beam as from a projector or from a laser and an expander. Light passing through the breast is detected by either a contact detector or by a television camera. However, since collimated light is used for illumination, both detection methods provide only a shadowgraph of the breast.

In summary, the prior art may be divided into two broad categories. A first category of prior art systems images shadowgraphs of the breast without substantial specificity as to the depth. The second category focuses beams on a point in the breast and requires scanning to image the breast.

In general methods of detecting cancer in the breast using transillumination, use red visible light and/or infrared light, generally to detect patterns of increased vascularity which surrounds breast cancer. It is believed that such light is used because light (other than red) in the visible range is strongly attenuated by body tissues (especially by the blood).

SUMMARY OF THE INVENTION

The present invention is directed to non-ionizing radiation imaging system especially useful for mammography.

One aspect of some preferred embodiments of the invention provides for imaging of planes of the breast utilizing non-ionizing radiation. The advantages of this aspect of the invention is that it significantly reduces the effects of overlying and underlying structures in selectively imaging a plane of the breast, rather than imaging a shadowgraph. This is facilitated through the use of a special contact window primarily located between radiation detectors and tissue being imaged and by the use of a camera focused on a depth of a slice to be imaged.

In addition, in accordance with an aspect of some preferred embodiments of the invention, light in ranges other than red is used to image the breast. In particular, light of various limited ranges of wavelengths is used to selectively image the breast. The limitation takes advantage of the fact that different anatomical structures absorb different wave lengths of light energy to different extents. Breasts consist in large proportion of fatty tissue. The range of wave lengths used, i.e. 490–670 nanometers is centered around the wave length of minimal optical absorbency of the fatty tissue in order to assure sufficient light transmission for detection. In this wave length range the absorbency differences, i.e., the contrast between the different tissue types is much higher than it is in the infrared region used extensively in the prior art. Successful imaging in this wave length region, is surprising since the overall transparency in that region is very low. However, it has been found that despite the fact that only a low light intensity comes through, nonetheless cross sectional images with clearly recognizable anatomical details are obtained because of the relatively high contrasts. The details are improved when using the special contact window to reduce to a large extent interfering light scattering of the tissue at the skin to air interface.

In preferred embodiments of the invention the detector focuses on different planes of the breast per imaging scan. Each of the planes are then preferably imaged, using different wave lengths of light, to provide increased diagnostic information.

In a further preferred embodiment of the invention, stereoscopic imaging, utilizing one or both of the above aspects of the invention is provided. This is accomplished by obtaining multiple images of the same plane observed from different angles.

There is thus provided, in accordance with a preferred embodiment of the invention, apparatus for imaging cross sectional views of the inner structure of the breast, the apparatus comprising:
- a source of light, illuminating the breast, situated at a first position of the breast;
- a matching interface situated, at a second position, on a surface of the breast, which reduces scatter caused by said surface; and
- an imaging detector focused on a plane within the breast, through said matching interface.

Preferably, is configured with lenses to provide a selectable plane in the breast to be imaged on the detector. Preferably, the lenses provide a narrow depth of field.

In a preferred embodiment of the invention, the matching interface comprises a surface of a transparent non-porous material and the breast.

Preferably, the imaging detector comprises one or more of a matrix detector, a video camera, a CCD array and a photographic film.

In a preferred embodiment of the invention the apparatus includes an optical filter situated between the source and the detector that limits the light reaching the detector from the source to a visible spectral band excluding red.

There is further provided, in accordance with a preferred embodiment of the invention apparatus for imaging of the inner structure of the breast, the apparatus comprising:
- a source of light illuminating the breast situated at a first position of the breast;
- a detector situated at a second position relative to the breast, said detector detecting light from said source passing through a portion of the breast from the source; and
- an optical filter situated between source and the detector that limits the light reaching the detector from the source to a visible spectral band excluding red.

Preferably, the optical filter has a lower pass-band limit of 520 nanometers or more and an upper pass-band limit of 580 nanometers or less. Alternatively the optical filter has a lower pass-band limit of 490 nanometers or more and an upper band-pass limit of 510 nanometers or less.

In a preferred embodiment of the invention, the apparatus includes:
- a plurality of optical filters;
- a filter holder situated between the source and the detector, such that when a filter is placed in said holder light reaching the detector from the source is limited to a visible spectral band different from that of at least one of the other filters and wherein at least one of the filters transmits in a range outside the red and infra-red; and
- means for selectively changing the filter in the holder.

There is further provided, in accordance with a preferred embodiment of the invention apparatus for imaging of the inner structure of the breast, the apparatus comprising:
- a source of light illuminating the breast situated at a first position of the breast;
- a detector situated at a second position relative to the breast, said detector detecting light from said source passing through a portion of the breast from the source;
- a plurality of optical filters;
- a filter holder situated between the source and the detector, such that when a filter is placed in said holder light reaching the detector from the source is limited to a visible spectral band different from that of at least one of the other filters and wherein at least one of the filters transmits in a visible range outside the red and infra-red; and
- means for selectively changing the filter in the holder.

In a preferred embodiment of the invention, at least one of the filters has a lower pass-band limit of 520 nanometers or more and an upper pass-band limit of 580 nanometers or less.

In a preferred embodiment of the invention, at least one of the filters has a lower pass-band limit of 490 nanometers or more and an upper pass-band limit of 510 nanometers or less.

In a preferred embodiment of the invention, at least one of the filters has a lower pass band limit greater than 620 nanometers.

In a preferred embodiment of the invention the source of light comprises an incandescent light source. Alternatively or additionally the source of light comprises a high intensity discharge light source.

In a preferred embodiment of the invention, the source of light is a laser source having an output in the visible spectral band excluding red.

There is further provided, in accordance with a preferred embodiment of the invention, apparatus for imaging of the inner structure of the breast, the apparatus comprising:

a source of laser light having an output in the visible spectral band excluding red illuminating the breast situated at a first position of the breast; and a detector situated at a second position relative to the breast, said detector detecting light from said source passing through a portion of the breast from the source.

In a preferred embodiment of the invention, the source of laser light has an output at between 490 and 510 nanometers. Alternatively or additionally, the source of laser light has an output at between 520 and 580 nanometers. Alternatively, the laser source provides a tunable laser output. Preferably, the laser is tunable to a wavelength above 620 nanometers.

There is further provided, in accordance with a preferred embodiment of the invention, apparatus for obtaining stereotactic images of the interior of a breast, comprising:

at least one source of light illuminating the breast and situated at a first position of the breast;

at least one matching interface situated, at a second position, on a surface of the breast, which reduces scatter caused by said surface; and a pair of spaced imaging detectors that view a portion of the breast through said at least one interface and produce images of said portion;

means for viewing the images such that a sterotactic image is perceived by a viewer.

Preferably, the apparatus includes an optical arrangement for focusing each of the detectors on a same region in the interior of the breast.

Preferably, the matching interface comprises a surface of a transparent non-porous material and the breast.

In various preferred embodiments of the invention the imaging detectors comprise one or more of matrix detectors, video cameras, CCD arrays and photographic film.

In a preferred embodiment of the invention, the apparatus includes a breast cage for supporting the breast during imaging.

There is further provided, in accordance with a preferred embodiment of the invention, a method of imaging the breast comprising:

illuminating the breast;

reducing interface light scatter generation at a portion of the surface of the breast; and selectively imaging a slice in the breast through the portion.

In a preferred embodiment of the invention, the method includes imaging a plurality of slices within the breast. Preferably, imaging a plurality of slices comprises imaging slices at angles to each other. Alternatively or additionally, imaging slices comprises imaging slices from different vantage points outside the breast.

In a preferred embodiment of the invention the method includes producing a three dimensional image from said multiple images.

In a preferred embodiment of the invention, the method includes correcting one of said images based on at least a second one of said images. In various preferred embodiments of the invention correcting comprises one or more of correcting for background and scattered light, and correcting for unfocused light from overlying and underlying structures.

In a preferred embodiment of the invention, correcting comprises:

imaging a slice from two slightly different vantage points; and reducing the effects of scatter from one of the images based on the other of the images.

In a preferred embodiment of the invention the method includes limiting the light used for imaging to a visible spectral band excluding red.

There is further provided, in accordance with a preferred embodiment of the invention, a method of imaging the breast comprising:

illuminating the breast;

forming an image of said illumination passing through a portion of the breast; and limiting the light used for imaging to a visible spectral band excluding red.

In a preferred embodiment of the invention, the visible spectral band is limited to a band having a lower band limit of at least 520 nanometers and an upper band limit of below 580 nanometers. Alternatively, the visible spectral band is limited to a band having a lower band limit of at least 490 nanometers and an upper band limit of below 510 nanometers.

In a preferred embodiment of the invention, the method includes separately imaging the breast at a plurality of wavelengths or wavelength bands, at least one of which encompasses a range outside the red and infra-red.

There is further provided, in accordance with a preferred embodiment of the invention, a method of imaging the breast comprising:

illuminating the breast; and separately imaging the breast at a plurality of wavelengths or wavelength bands, at least one of which encompasses a range outside the red and infra-red.

In a preferred embodiment of the invention at least one of the images is generated from light having wavelengths between 520 nanometers and 580 nanometers.

In a preferred embodiment of the invention at least one of the images is generated from light having wavelengths between 490 nanometers and 510 nanometers.

In a preferred embodiment of the invention at least one of the images is generated from light having a wavelength greater than 620 nanometers.

In a preferred embodiment of the invention, the method includes utilizing wavelengths of light in producing images such that larger blood vessels are emphasized. Alternatively or additionally, the method includes utilizing wavelengths of light in producing images such that fine blood vessels are emphasized. Alternatively or additionally the method includes utilizing wavelengths of light in producing images such that tumor tissue is emphasized.

BRIEF DESCRIPTION OF THE DRAWINGS

The foregoing and other objects, features and advantages of the invention will be best understood from the following detailed description of preferred embodiments of the invention taken with reference to the accompanying drawings, in which the same reference numbers are used to describe the same or similar structures in the drawings and in which.

DETAILED DESCRIPTION OF PREFERRED EMBODIMENTS OF THE INVENTION

Figure 1A:
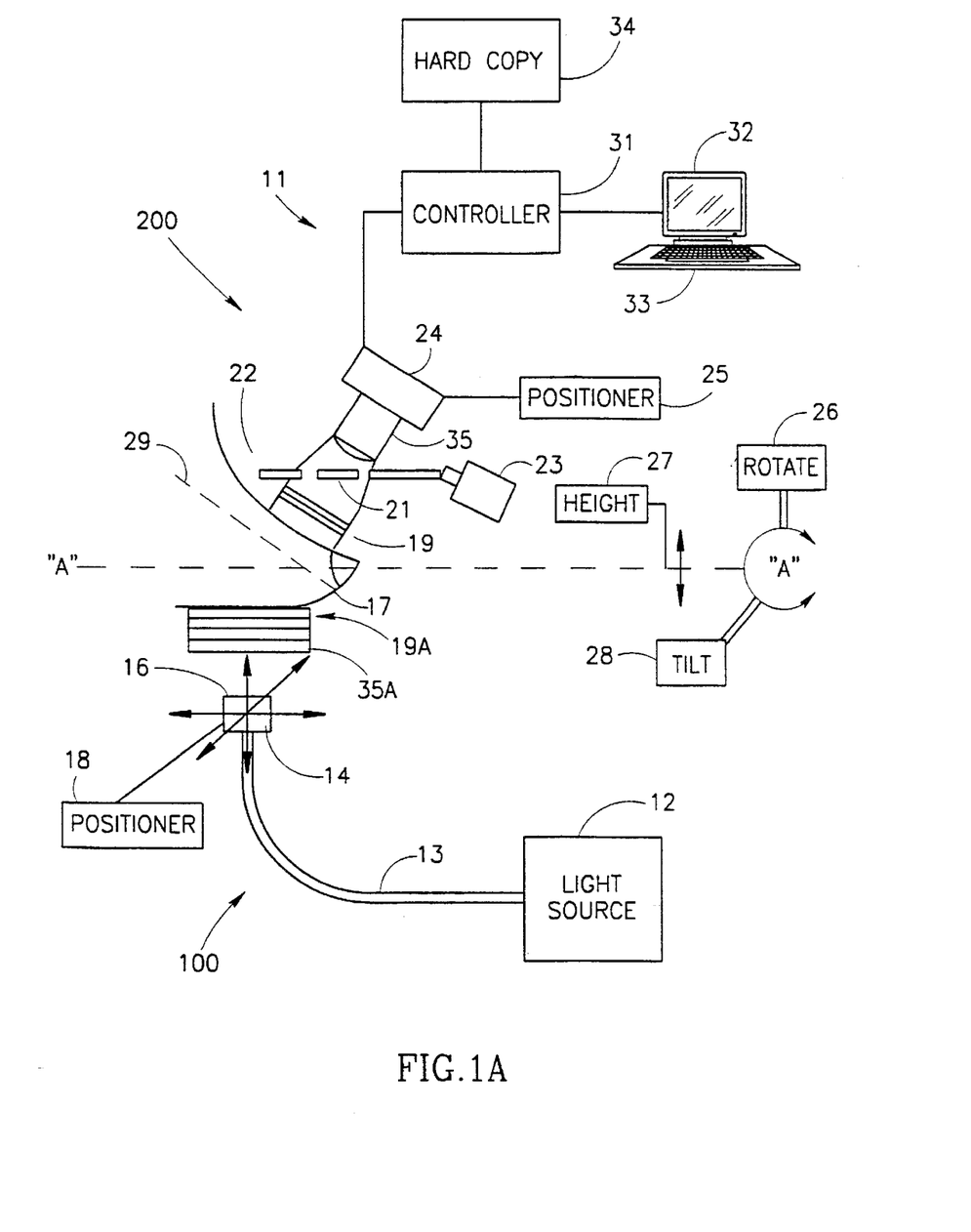
FIG. 1A is a schematic partially block diagram showing of an optical mammography system, in accordance with a preferred embodiment of the invention.

FIG. 1A Is a schematic illustration of a preferred embodiment of a transillumination imaging system 11, in accordance with a preferred embodiment of the invention. System 11 comprises two main parts, a light source portion 100 and a detector portion 200.

Light source portion 200 preferably includes a light source 12 connected by optical fibers such as optical fiber indicated at 13, that extends through a fiber holder block 14 so that the end of the fiber, such as end 16, is proximate to the breast 17 being examined.

The light source may be a laser source or a high intensity light source such as a xenon arc lamp or a halide lamp. The fiber holder is positioned through a fiber positioner 18, so that the fiber or fibers illuminate a volume within the breast. It should be pointed out that, preferably, the light source does not provide collimated illumination of the breast. Furthermore, while source portion 100 as shown in FIG. 1A is preferred, in other preferred embodiments of the invention, any strong light sources at appropriate wavelengths may be used.

The light from source portion 100 transverses the breast and passes through a light scatter minimizer such as a contact window 19 which is in contact with the breast generally opposite to where the light enters the breast.

The contact window is designed to minimize to a great extent the scatter of light that normally occurs at the-skin air interface. It has been found that the use of the contact window enables focusing to within the breast to allow for at least partially selective images of slices (29) of the breast.

Light passing through the contact window passes through a selected filter such as band pass filter 21 selected out of filter cartridge 22, preferably containing a plurality of filters. The filters are preferably selected using the filter selector 23, however, any method known in the art, including manual changing of filters may be employed. The selected band pass filter limits the band pass of the light passing therethrough to a range such that the light provides an image emphasizing either:

1) the fine vascular vessels;
2) actual tumor tissues; or
3) the large vascular vessels that are usually associated with tumors.

After passing through the filter, the light enters into a detector device such as detector 24. The detector can be a CCD camera, a photographic camera using film, a vidicom, a video camera or a, preferably dense, array photoelectric cells, for example. Detector 24 is positioned by the camera positioner 25 which can move the camera in the X and Y directions where X and Y are orthogonal directions in the plane of the detector (X being parallel to the plane of the drawing) and Z extends into and out of the breast along the optical axis of the detector.

Preferably, a rotator 26 is provided which can rotate the camera and associated structure around an axis "A", preferably through the axis of the breast. A height adjuster 27 is preferably provided to moves the camera and associated structure up or down. A tilter 28 is preferably provided to tilt the orientation of the camera about its axis and to tilt the rotational axis "A." This combination of changes in position and orientation allow for imaging in a variety of directions into the breast (and thus for imaging any plane in these directions) and for assuring that the contact plate remains in contact with the breast. Elements 26, 27 and 28 are shown in an inset to the right of the main drawing of FIG. 1A.

The output of the detector 24 feeds into a computer controller 31. The computer-controller processes the detector data to provide imaging data to imaging display 32 and/or to a hardcopy device 34. The combination computer controller and display 32 is shown having an operator input such as a key-board shown at 33. In a preferred embodiment the detector device 24 operates in conjunction with a lens 35 to focus on selected planes (29) in the breast. By focusing on different planes any lesion or tumorous growth is located as being in a particular plane and the time to locate the lesion is shortened appreciably. Furthermore, such focusing reduces the effect of structure overlying and underlying the plane since only objects in the plane are in focus. Preferably, lens 35 has a limited depth of focus to emphasize a given plane (29).

In other preferred embodiments of the invention, contact plate 19 is placed in contact with the breast and the optics of the camera are not mechanically linked to the contact plate. In such systems, the breast is preferably compressed by the contact plate and by a similar plate on the light input side of the breast. Such compression of the breast in transillumination is well known for shadowgraph systems.

The lighting of the breast is shown as not being in line with the optical axis of the detector. While not necessary, in line illumination may also be used.

In one embodiment a contact window 19A is also used on the light input side of the breast. Lens 35 and may also optionally be used to focus the light onto the plane selected by lens 35.

Figure 1B:
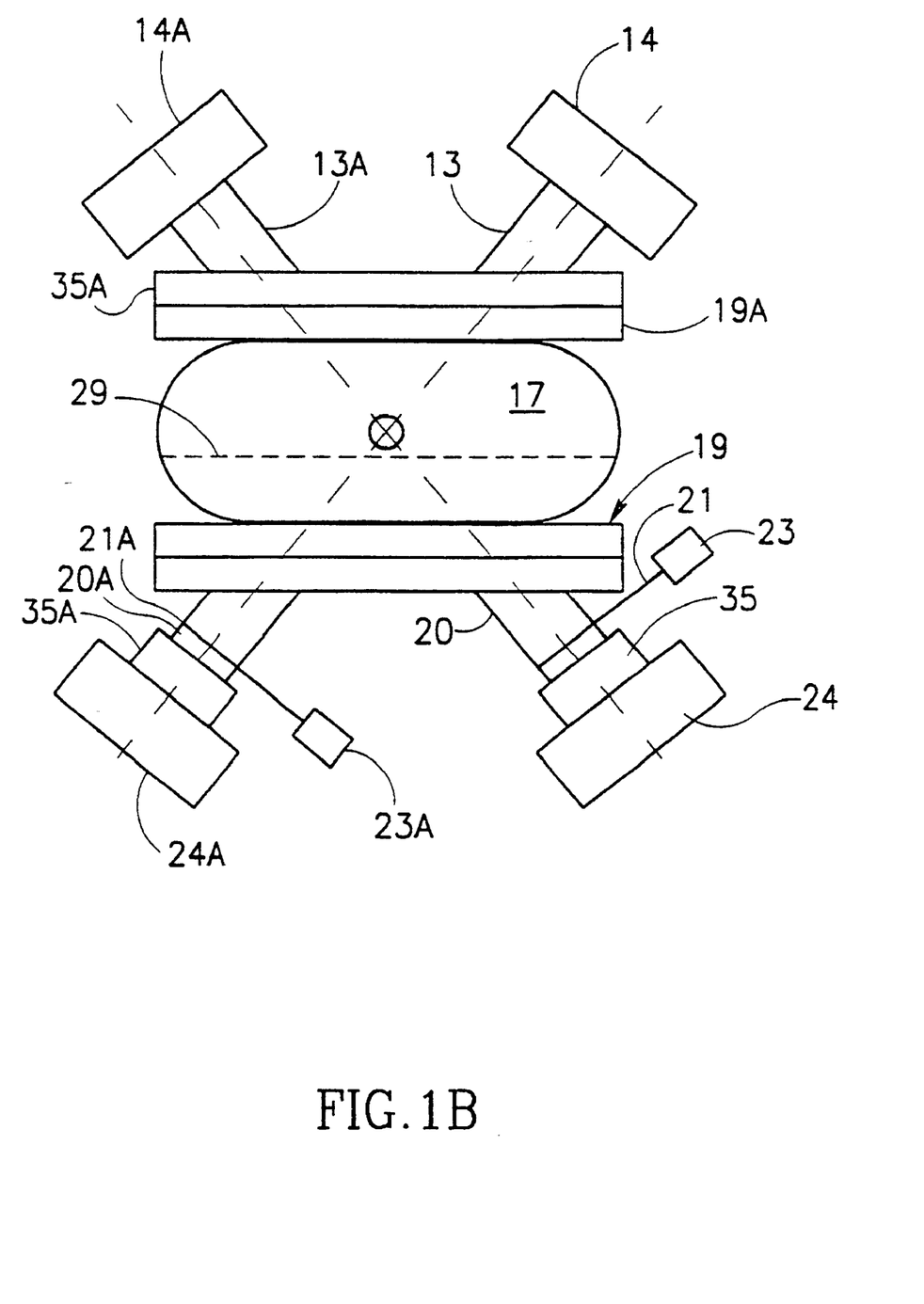
FIG. 1B is a schematic front view, block diagram showing the optical mammography system of FIG. 1A configured for stereoscopic imaging.

FIG. 1B illustrates a stereotactic imaging system, in accordance with a preferred embodiment of the invention. A light source (not shown) is coupled to a pair of optical fibers 13, 13a spaced apart and positioned by fiber positioners (not shown) attached to holder blocks 14, 14a. FIG. 1B shows a contact window 19a selectively positioned on the light input side of the breast and a lens 35a optionally located on the light input side of the breast. These components operate as described with relation to FIG. 1A. Preferably, only one of the light sources is illuminated at one time. Alternatively, only a single central light source is utilized for acquiring both images. Further, while the detector axes are shown at an acute angle, parallel axes of spaced detectors are also suitable for stereo imaging.

Alternatively, stereoscopic images can be generated is a system in which the breast is firmly held by contact plates, by moving the camera (and optionally, the light source) laterally to its axis and acquiring a second image at the second position.

A contact window is located on the light output side of the breast. A pair of shrouds or light shields 20, 20a are positioned to shield detectors 24, 24a from light not coming from the optical fibers through the breast. The light from the optical fibers goes through selected filters 21, 21a and lenses 35, 35a to the detectors such as cameras 24, 24a. These components also act as described with regard to FIG. 1A.

In general, for stereoscopic imaging a longer depth of focus is used than for planar imaging, such that a volume which is in focus for both cameras, is imaged in stereo.

Such stereoscopic images may be viewed using any of the many methods of viewing of said images as known in the art.

Figure 2:
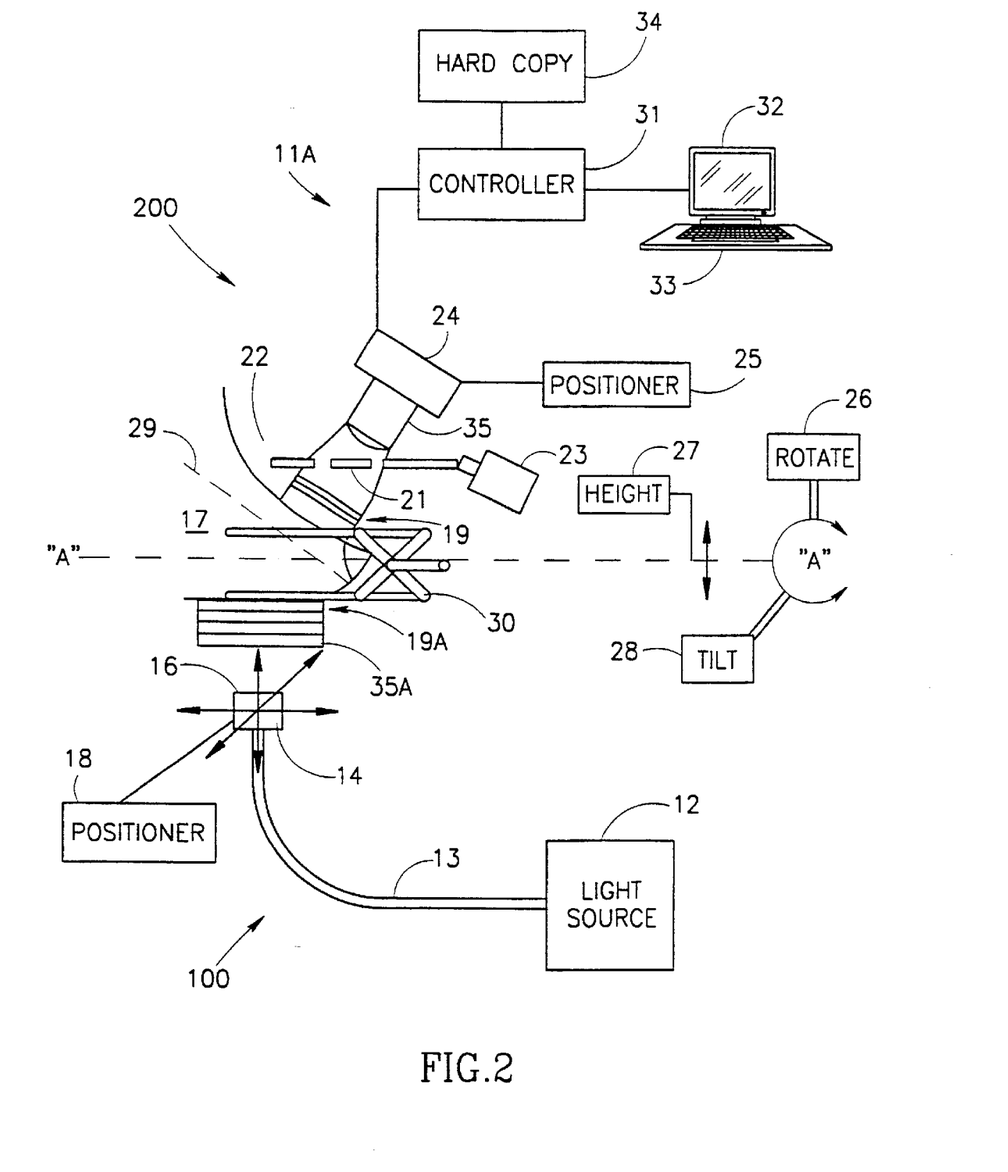
FIG. 2 shows a preferred embodiment of an optical mammography system including a breast support cage.

A second preferred transillumination system 11A is shown in FIG. 2. System 11A includes all of the same components shown in FIG. 1A. In addition it provides a breast support cage 30 which is used to support the breast during the imaging procedure. Support cage 30 supports the breast and at the same time enables good contact with the breast for imaging.

Figure 3:
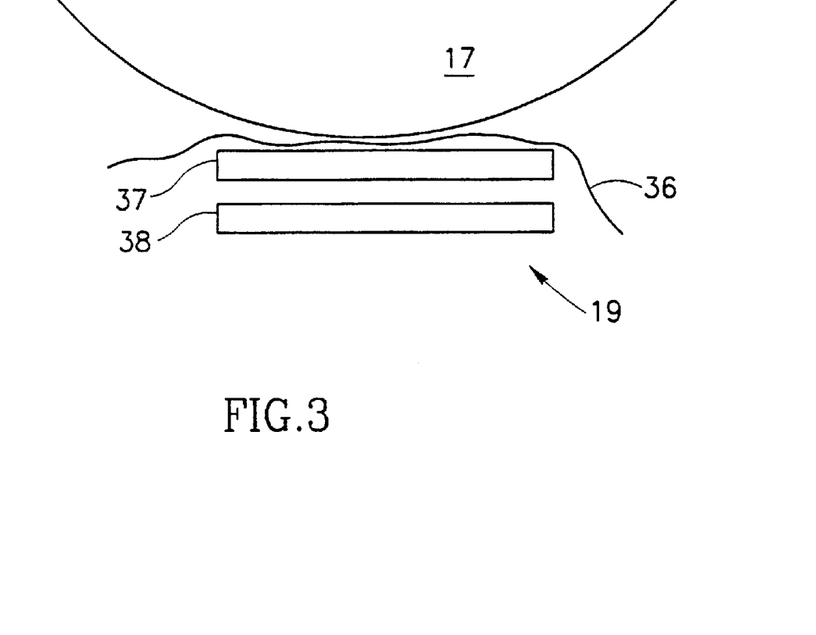
FIG. 3 shows details of a contact window used, in accordance with preferred embodiments of the invention, to dramatically reduce the scatter at the skin to air interface.

Details of contact window 19, in accordance with a preferred embodiment of the invention, are shown in FIG. 3. Window 19 comprises a non-porous sheet material 36 which is held contiguous to the breast 17 and supported by a transparent support plate 37. Optionally, the contact window includes a light filter 38 which provides preliminarily filtration of the light illuminating the breast, preferably to be between 400 to 800 nanometers The contact window dramatically decreases scatter at the skin-air interface. The reduction in scatter enables operating successfully at light frequencies not considered by the prior art. The support plate is also used as a compression plate to compress the breast to further reduce scatter.

Alternatively, the sheet 36 may be omitted and a non-porous plate 37 provided. However, a sheet 36 is preferred since it promotes sweating (and an improved interface) and provides a disposable interface, important for hygienic reasons.

When the skin is in contact with the non-porous material; which may be a soft or a hard transparent plastic material, or even a rigid transparent material such as rigid plastic or glass, then the light scattering of the interface of the skin and air is reduced in the 500 and 800 nanometers wavelength band. The dramatic reduction of light scattering comes about because when the skin of the breast has come into contact with the non-porous material a thin layer of perspiration is secreted as a result of a local temperature rise. The layer of perspiration which fills the gap between the transparent covering and the skin results in greatly reduced light scattering at the interface. It is believed that in the absence of such an interface, only a shadowgraph of the breast is possible. since the skin-air interface acts in much the same way as a "ground glass" would in ordinary imaging.

In preferred embodiments of the invention images of a plurality of slices are acquired. These images may be parallel to each other and may then be used to construct a three-dimensional image of at least a portion of the breast. Since each of the images is formed of a first, in-focus part (the slice itself) and a second, out-of-focus, part caused by overlying and underlying structures. Using methods known in the art, the images can be partially corrected for the effects of overlying and underlying structures.

Furthermore, slices may be acquired from different vantage points. One such embodiment was described above with respect to FIG. 1B. It is also possible to acquire two or more images of the same slice from very slightly different angles or vantage points. These images will have almost identical slice image portions. However, due to the fact that the scatter varies with angle in a random-like manner, the scatter contribution is different for each of the images. Thus, if these images are added, the resulting image will have suppressed effect of scatter, as compared to a single image.

Figure 4:
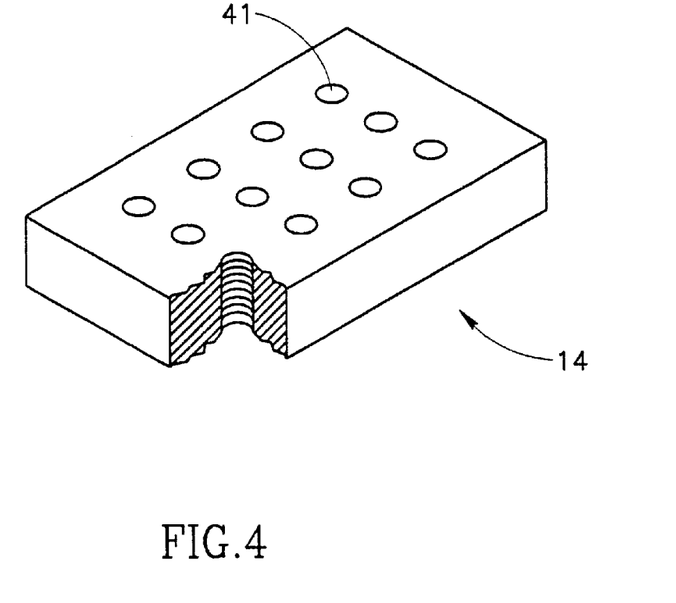
FIG. 4 is a pictorial showing of an optical fiber holding block used in the system.

FIG. 4 shows details of a preferred embodiment of optical fiber holder block 14. As shown herein the, fiber holder block comprises a plurality of apertures such as aperture 41. The multiplicity of apertures indicates that a plurality of optical fibers can be held at one time in the holder and used to provide sufficient illumination or illumination by light beams spread over a large volume so that a planar surface can be focused upon within the widely projected light beam. The placement of the light source may also be effected by switching the light source between different fibers.

Figure 5:
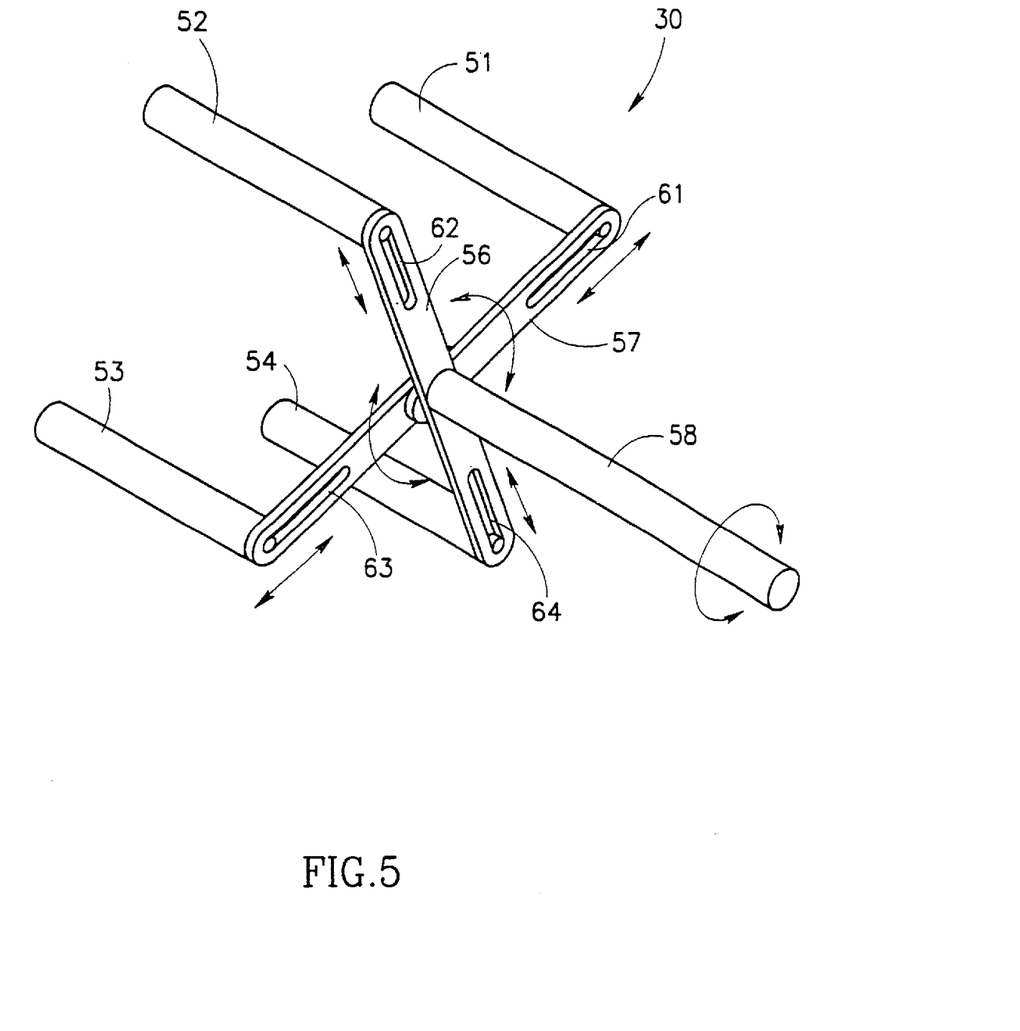
FIG. 5 shows details of the breast support cage shown in FIG. 2.

An exemplary preferred embodiment of breast support cage 30 is shown in detail pictorially in FIG. 5. The exemplary support cage comprises four horizontally extending legs 51, 52, 53 and 54. The legs are preferably at angles to each other and these angles are preferably adjustable. The legs are preferably held by transverse members 56 and 57. The transverse members are preferably held by a horizontally extending handle member 58. It is possible to move the transverse members 56, 57 relative to each other depending upon the size and the shape of the breast being caged. Similarly, each of the horizontally extending legs 51–54 can be individually moved towards and away from the axis of the handle 58, for example within slots 61, 62, 63, 64 in the transverse members. The legs can then be fastened at the moved position, for example, by screws or wing nuts (not shown). Thus the cage is readily adaptable for almost any size or shape of breast being examined. The cage also enables contact between breast 17 and optical fiber 13 and between breast 17 and camera 24 through contact window 19.

Figure 6:
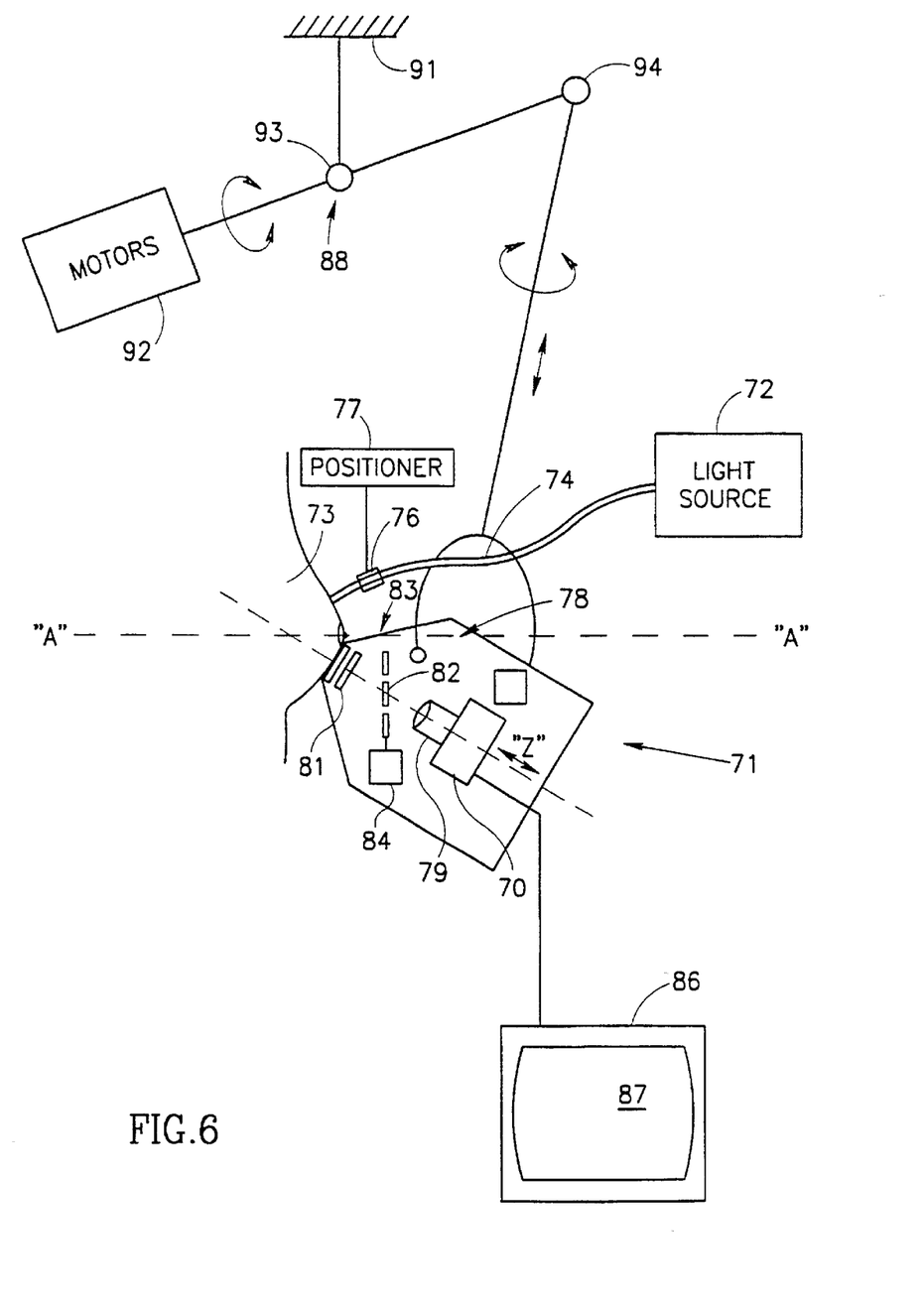
FIG. 6 shows another preferred embodiment of an optical mammography system in accordance with the invention when used for imaging small breasts.

FIG. 6 schematically shows another embodiment of a transillumination system 71 in accordance with a preferred embodiment of the invention. System 71 is particularly useful for imaging small breasts. It preferably includes a light source 72 which provides light to the breast 73 through semi-rigid optical fiber 74. The optical fiber is shown being held in a fiber holder 76 attached to a fiber positioner 77. The positioner positions the fiber to transmit light to a breast optionally through a contact window, not shown.

A preferred detector arrangement is shown at 78. It preferably includes a detector 70 for acquiring light that has traversed the breast and passed through a lens system indicated at 79. The light from the breast is received through a contact window 81 (similar to window 19 described above) and a selected filter 82 out of a range of filter in a filter cartridge indicated at 83. The filter to be used is selected by a filter selector 84. The system is under the control of a computer controller 86 which includes the display means 87.

The detector arrangement is coupled to a support indicated at 88 which enables movement of system 71 all directions. The support is coupled to a stationary object such as a ceiling 91. The system is rotated using a combination of linear and rotating motor, both of which are schematically indicated at 92, coupled through pivot points 93 and 94 to enable movement in all directions. It should be understood that the supports and motivating motor schematically depict a system for moving the detector in any manner well known to those skilled in the art. Preferably, the system shown (and other structure not shown) provides all of the movements described in respect to the preferred embodiment of FIG. 1A.

Figure 7:
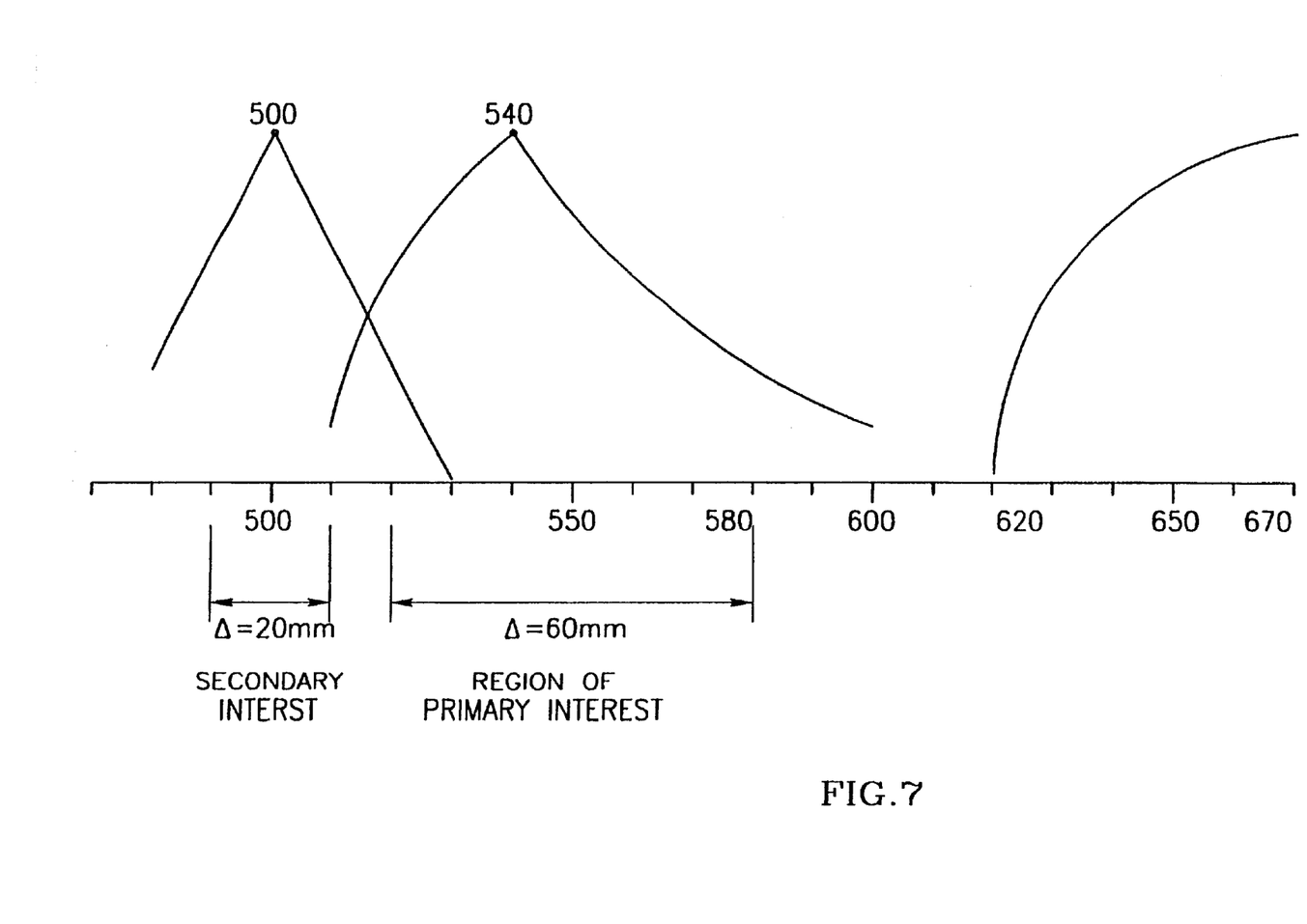
FIG. 7 is a graphical showing of the non-ionizing radiation wavelength regions of interest used in preferred embodiments of the invention.

FIG. 7 is a graphical showing of the regions of interest defined by the wavelengths of the non-ionizing radiation. The graph shows that from approximately 490 nanometers to approximately 510 nanometers fine blood vessels and fat are ideally imaged. This generally an area of secondary interest. A region of primary interest is shown to be from 520 to 580 nanometers. Tumor tissue is ideally imaged in that range of wavelengths and most preferably in the range near 540 nanometers, for example 530 to 550 nanometers. High structural definition is obtained in both the primary and secondary regions of interest.

The third region of interest extends from approximately 620 nanometers and greater. Larger veins and arteries are imaged, a multiplicity of such veins and arteries are often indicative of cancerous tissue. This is the region generally imaged in prior art systems. While it does provide some information as to vascularity, it does not provide the information available from images in the primary and secondary regions of interest. Using this knowledge the system uses wavelength filters designed for obtaining images preferably within these three regions of interest and significantly in one or both of the lower wavelength regions.

The filters used along with the contact windows reduce the scatter dramatically, since scatter outside the band of interest is completely removed. The apparatus takes advantage of the fact that different anatomical structure absorbs different wavelengths of light to different extents as shown in FIG. 7. As the breast consists of a large proportion of fatty tissue, the wavelength bands used are around the wavelength of minimal optical absorbence by the fatty tissue in order to facilitate sufficient light transmission for detection. In this wavelength region even though the absorbence differences, i.e., contrast between the different type of tissues are much higher than it is in the infrared region the overall transparency is very low, due to the high blood absorbance at these wavelengths. Surprisingly however, despite the fact that the light intensity is low the high contrast provides images with clearly recognizable anatomical details. However, high intensity light and/or highly sensitive film or detectors and/or long exposure times may be required.

Alternatively, the light source may be a laser light source having an output in region of primary interest and/or in the region of secondary interest. Alternatively, it may be a tunable laser having outputs in these ranges.

While the invention has been described in terms of the preferred embodiments, those skilled in the art will recognize that the scatter reducing mechanisms can be varied and the detectors can be varied within the spirit and scope of the dependent claims.

I claim:

1. Apparatus for imaging cross sectional views of the inner structure of a breast, the apparatus comprising:
   a source of light, illuminating the breast, when the source of light is situated at a first position of the breast;
   a matching interface which, when situated at a second position on a surface of the breast, reduces scatter caused by said surface;
   an imaging detector that forms a two dimensional image responsive to light incident thereon, the detector receiving light through the matching interface; and
   optics that focuses an image of a plane within the breast, through said matching interface onto the imaging detector, to form an image thereon, such that the detector produces a two dimensional image corresponding to an image of the plane, responsive to light incident thereon.

2. Apparatus according to claim 1 wherein said optics comprises lenses to provide a selectable plane in the breast to be imaged on the detector.

3. Apparatus according to claim 2 wherein the lenses provide a narrow depth of field.

4. Apparatus according to claim 1 wherein the matching interface comprises a surface of a transparent non-porous material and the breast.

5. Apparatus according to claim 1 wherein the imaging detector comprises a matrix detector.

6. Apparatus according to claim 1 wherein the imaging detector comprises a video camera.

7. Apparatus according to claim 1 wherein the imaging detector comprises a CCD array.

8. Apparatus according to claim 1 wherein the imaging detector is a photographic film.

9. Apparatus according to claim 1 wherein the illumination is not focused onto the plane.

10. Apparatus according to claim 1 wherein the source of light comprises
    a non-laser radiant source; and at least one optical fiber situated between source and the detector that limits the light reaching the detector from the source to a visible spectral band limited to wavelengths in the range from 490 to 510 manometers or 520 to 580 nanometers; or
    a source of laser light has an output at between 490 and 510 nanometers or between 520 and 580 nanometers or is a tunable light source.

11. Apparatus according to claim 1 wherein the source of light comprises a high intensity discharge light source.

12. Apparatus according to claim 1 and including a breast cage for supporting the breast during imaging.

13. A method of imaging a breast comprising:
    illuminating the breast;
    reducing interface light scatter generation at a portion of the surface of the breast; and
    imaging a slice through the breast, including:
        focusing a two dimensional image of a slice through the breast onto imaging detector; and
        detecting a two dimensional image corresponding to an image of the slice, from the response of the detector to the formed image.

14. A method according to claim 13 and including imaging a plurality of slices within the breast.

15. A method according to claim 14 wherein imaging a plurality of slices comprises imaging slices at angles to each other.

16. A method according to claim 14 wherein imaging slices comprises imaging slices from different vantage points outside the breast.

17. A method according to claim 13 and including:
    producing a three dimensional image from said multiple images.

18. A method according to claim 13 and including:
    correcting one of said images based on at least a second one of said images.

19. A method according to claim 18 wherein correcting comprises correcting for background and scattered light.

20. A method according to claim 18 wherein correcting comprises correcting for unfocused light from overlying and underlying structures.

21. A method according to claim 18 wherein correcting comprises
    imaging a slice from two slightly different vantage points; and
    reducing the effects of scatter from one of the images based on the other of the images.

22. A method according to claim 13 wherein the illumination is not focused onto the plane of the slice.

23. A method according to claim 13 and comprising:
    limiting the light used for imaging to a visible spectral band excluding red.

24. A method according to claim 23 wherein the visible spectral band is limited to a band having a lower band limit of at least 520 nanometers and an upper band limit of below 580 nanometers.

25. A method according to claim 23 wherein the visible spectral band is limited to a band having a lower band limit of at least 490 nanometers and an upper band limit of below 510 nanometers.

26. A method according to claim 13, including:

providing wavelengths at which larger blood vessels are emphasized, wherein illuminating comprises illuminating with said provided wavelengths to generate an image in which larger blood vessels are emphasized.

27. A method according to claim 13, including:

providing wavelengths at which fine blood vessels are emphasized, wherein illuminating comprises illuminating with said provided wavelengths to generate an image in which fine blood vessels are emphasized.

28. A method according to claim 13, including:

providing wavelengths at which tumors are emphasized, wherein illuminating comprises illuminating with said provided wavelengths to generate an image in which tumors are emphasized.

* * * * *

UNITED STATES PATENT AND TRADEMARK OFFICE
CERTIFICATE OF CORRECTION

PATENT NO. : 6,668,187 B1
DATED : December 23, 2003
INVENTOR(S) : Asher Porath

It is certified that error appears in the above-identified patent and that said Letters Patent is hereby corrected as shown below:

Title page,
Item [86], "PCT No.: 371 (c)(1),(2),(4) Date: change "Jun" to -- Jan --
Item [56], References Cited, OTHER PUBLICATIONS, "Cutler, M.," reference, change "Transilluminations" to -- Transillumination as --

Signed and Sealed this

Fifth Day of October, 2004

JON W. DUDAS
*Director of the United States Patent and Trademark Office*